US00PP34721P2

(12) United States Plant Patent
Grosser

(10) Patent No.: US PP34,721 P2
(45) Date of Patent: Nov. 8, 2022

(54) SWEET ORANGE TREE NAMED 'OLL-20'

(50) Latin Name: *Citrus sinensis*
Varietal Denomination: OLL-20

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 29 days.

(21) Appl. No.: 17/221,056

(22) Filed: Apr. 2, 2021

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./202
CPC ..... A01H 6/785; A01H 5/08
See application file for complete search history.

(56) References Cited

U.S. PATENT DOCUMENTS

PP26,087 P3 11/2015 Grosser
PP27,829 P3 4/2017 Grosser

OTHER PUBLICATIONS

Neff. Citrus Industry Magazine, Nov. 8, 2019.*

* cited by examiner

*Primary Examiner* — Keith O. Robinson
(74) *Attorney, Agent, or Firm* — Dentons US LLP

(57) ABSTRACT

A new and distinct sweet orange clone 'OLL-20' has been developed from an unstable sweet orange selection designated as 'OLL', using tissue culture techniques. Undeveloped ovules from fruit of selection 'OLL' were cultured in vitro to generate an embryogenic callus, from which multiple independent clones were regenerated via somatic embryogenesis. Regenerated plantlets (somaclones) were grafted to UFR rootstocks and grown in the field for evaluation.

7 Drawing Sheets

Latin name of the genus and species of the plant claimed: *Citrus sinensis.*

Variety denomination: 'OLL-20'.

BACKGROUND OF THE INVENTION:

The present invention relates to a new and distinct variety of sweet orange tree (*Citrus sinensis*) named 'OLL-20'. 'OLL-20' is a somaclone regenerated from embryogenic callus (tissue culture) of 'Orie Lee Late' ('OLL') sweet orange (unpatented), with high quality fruit that usually matures in the standard 'Valencia' (unpatented) time period, but in some years a few weeks earlier. 'OLL' is believed to be an irradiation-induced mutant line thought to originate from 'Pineapple sweet orange' (not patented) in an abandoned USDA trial attempting to generate a seedless Pineapple. Recent molecular data supports a sweet orange origin, but could not confirm 'OLL' originated from Pineapple sweet orange. 'OLL' was not selected by any USDA scientists, but attracted attention because it never dropped fruit (a serious problem with Pineapple), and held quality late into the summer. Propagations of 'OLL' made by Dr. Jude W. Grosser were not uniform and included some trees of poor growth and productivity, as well as robust high-yielding trees.

In efforts to generate genetically stable clones from the OLL selection, tissue cultures (embryogenic callus) were established for the creation of somaclones. Among the OLL somaclones, 'OLL-20' showed a slightly earlier maturity in some seasons. True-to-typeness of 'OLL-20' was demonstrated by propagation via grafting on rootstocks 'UFR-2' (U.S. Plant Pat. No. 27,742), 'UFR-4' (U.S. Plant Pat. No. 27,745), 'UFR-5' (U.S. Plant Pat. No. 27,298) and 'UFR-6' (U.S. Plant Pat. No. 27,276) and planted at multiple locations (including Lee Groves in St. Cloud, Fla.). All propagated trees are stable and producing true-to-type fruit at multiple trial locations. 'OLL-20' was selected for release and commercialization due to its superior juice quality and flavor. The exceptional flavor of 'OLL-20' juice is supported by analytical data and organoleptic/flavor panel evaluations conducted by both the UF/CREC and Tropicana (PepsiCo.). 'OLL-20' yields are comparable to other commercial processing oranges, but slightly less than other released OLL clones 'OLL-4' (U.S. Plant Pat. No. 27,829) and 'OLL-8' (U.S. Plant Pat. No. 26,087). 'OLL-20' was first asexually propagated in St. Cloud, Fla., by traditional inverted T-bud grafting conducted in 2012 onto 18 rootstocks including commercial rootstocks 'Swingle' (not patented) and 'x639' (not patented), trees were planted in St. Cloud, Fla. in summer of 2013. All trees are producing true-to-type fruit.

SUMMARY OF THE INVENTION

Sweet orange selection 'OLL-20' produces round oranges with internal and external color significantly higher than that of standard 'Valencia' and often exceeds that of 'Rhode Red Valencia' (not patented). Fruit holds on the tree exceptionally well, and maintains quality into the summer. 'OLL' seedling trees (including 'OLL-20') have shown good drought tolerance in the greenhouse, as overgrown trees in small pots rarely wilt as compared to other sweet orange seedlings, and 'OLL' somaclone field trees in general have shown better cold-tolerance in the last two freezes than 'Valencia' trees in the same trial block. This apparent improved stress tolerance may be useful in the fight against Huanglongbing disease, as 'OLL-20' shows slightly better HLB tolerance than the standard Valencia sweet orange. Although minimal formal yield data is available, trees of 'OLL-20' appear to yield as good or better than standard 'Valencia'. The original 'OLL-20' tree yielded more than five 90 lb boxes of fruit in 2013 (8-year old tree). Sensory (taste panel) analyses have repeatedly indicated that 'OLL-20' juice from HLB+ trees has an exceptional flavor profile that exceeds that of the standard Valencia and even the other 'OLL' clones 'OLL-4' and 'OLL-8'. Juice from 'OLL-20' has been described as having a unique special floral bouquet. 'OLL-20' has excellent potential to improve the not-from-concentrate (NFC) portfolios of *Citrus* juice processors. Improved NFC orange juice flavor/quality is a way to help reverse declining orange juice consumption/sales. 'OLL-20' fruit generally has high juice content and good pounds solids. Like other OLL clones, 'OLL-20' peels easier than a standard 'Valencia', but still requires quadrant scoring for clean peeling when grown under Florida conditions.

Parent tree 'OLL' is a single tree (i.e., not a commercial variety) of which more than 50% of propagations using standard budwood did not grow off properly, resulting in trees of inferior horticultural quality with poor health, vigor, and productivity. 'OLL-20' is a somaclone produced from 'OLL', which has proven to be stable during standard propagation, with all propagated trees exhibiting normal health and vigor. 'OLL-20' shares many morphological characteristics with the original 'OLL' tree; however, the 'OLL-20' tree itself represents a significant improvement over the 'OLL' parent tree, since it can be stably propagated, unlike the original 'OLL' tree. Thus, 'OLL-20' can be distinguished from the original 'OLL' tree, at least, by its ability to be stably propagated by traditional grafting with 100% tree establishment success as opposed to approximately only 50% success from the original OLL tree 'OLL-20' can also be distinguished from other 'OLL' somaclones 'OLL-4' and 'OLL-8' by its unique and superior juice flavor; and, at least, by its trunk bark color, ovary diameter, and ovary color. 'OLL-20' can also be distinguished from 'OLL-4' and 'OLL-8' by its slightly earlier maturity. For the past two seasons, 'OLL-20' fruit matured 3-4 weeks earlier than fruit of both 'OLL-4' and 'OLL-8'. In the current season, 'OLL-20' juice had a mean brix/acid ratio (from fruit of 18 rootstocks) of 16.2 in mid-February whereas the mean ratios for 'OLL-4' and 'OLL-8' were 14.0 and 13.6, respectively.

BRIEF DESCRIPTION OF THE DRAWINGS

'OLL-20' is illustrated by the accompanying photographs, which show the tree's form, foliage and fruit. The colors shown are as true as can be reasonably obtained by conventional photographic procedures. The photographs are of a 'OLL-20' tree approximately 5-years old.

DETAILED BOTANICAL DESCRIPTION

Figure 1:
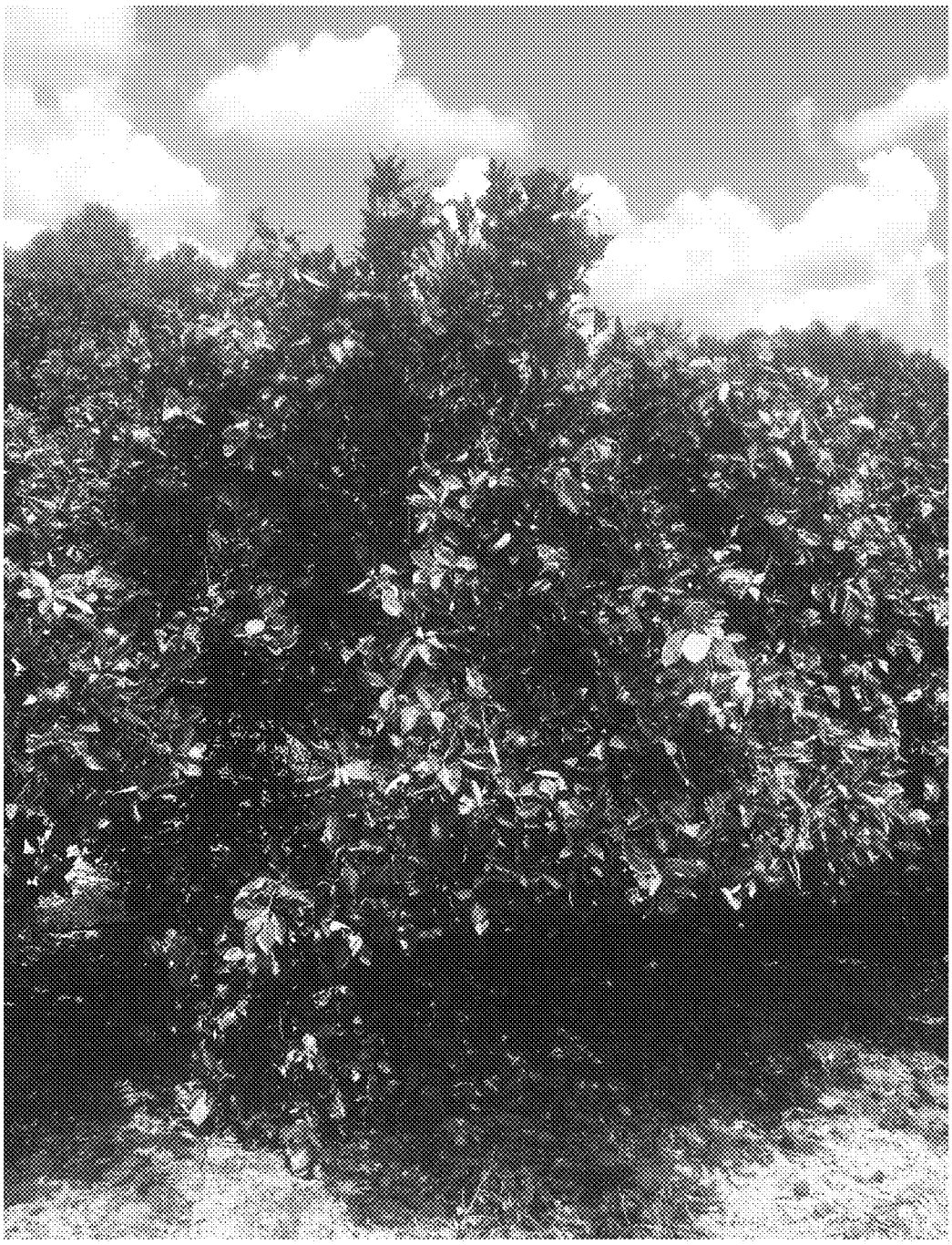
FIG. 1. Shows a 'OLL-20' tree on UFR-4 rootstock as well as the overall plant growth habit of 'OLL-20'.
Figure 2:
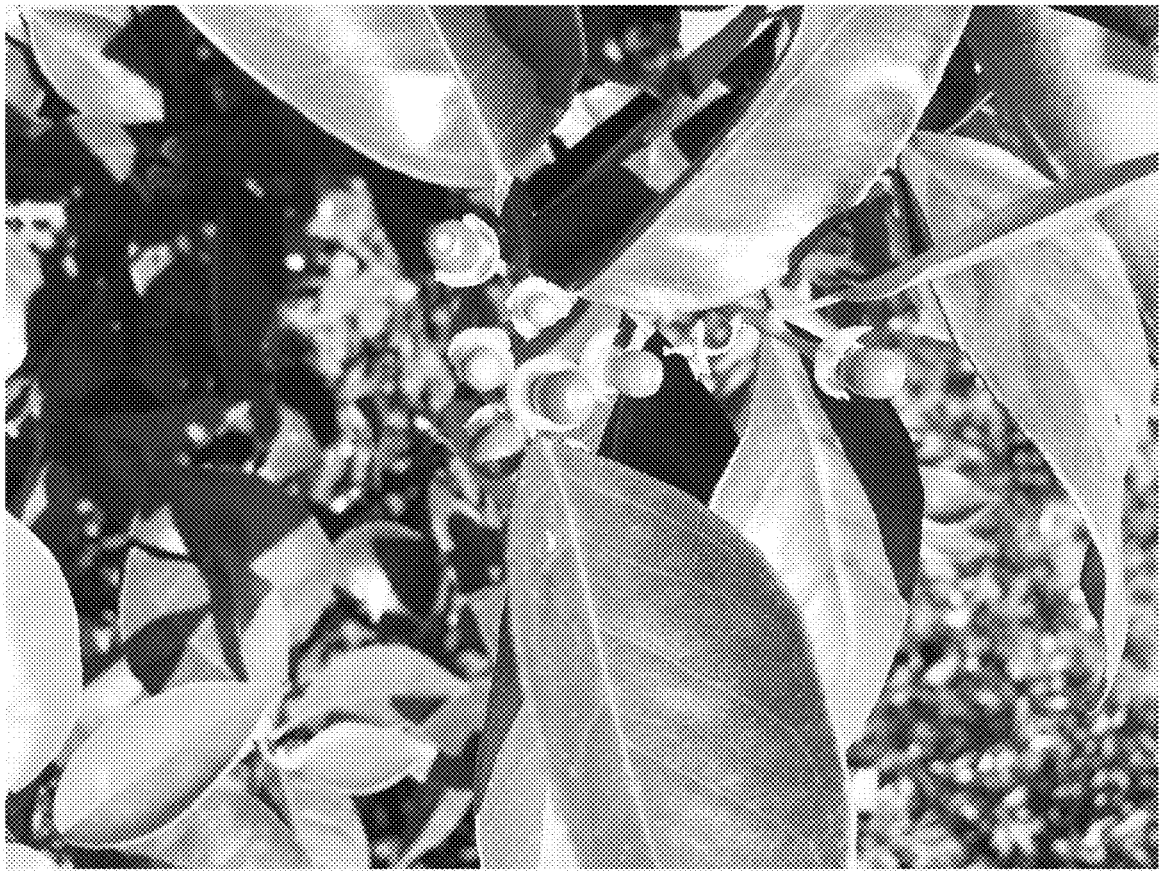
FIG. 2. Shows a close-up view of 'OLL-20' leaves and fruit set.
Figure 3:
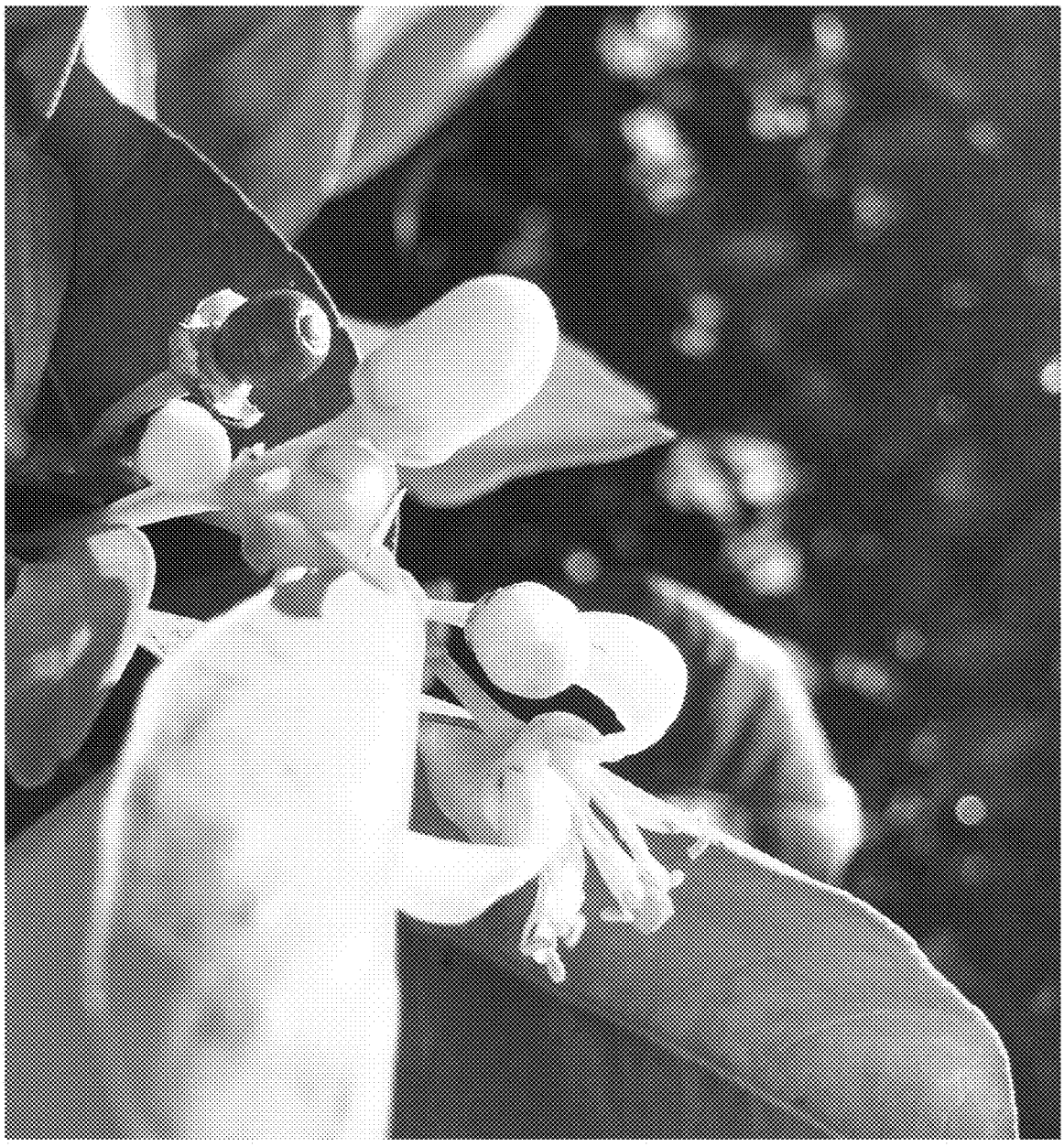
FIG. 3. Shows a close-up view of 'OLL-20' flowers and flower buds.
Figure 4:
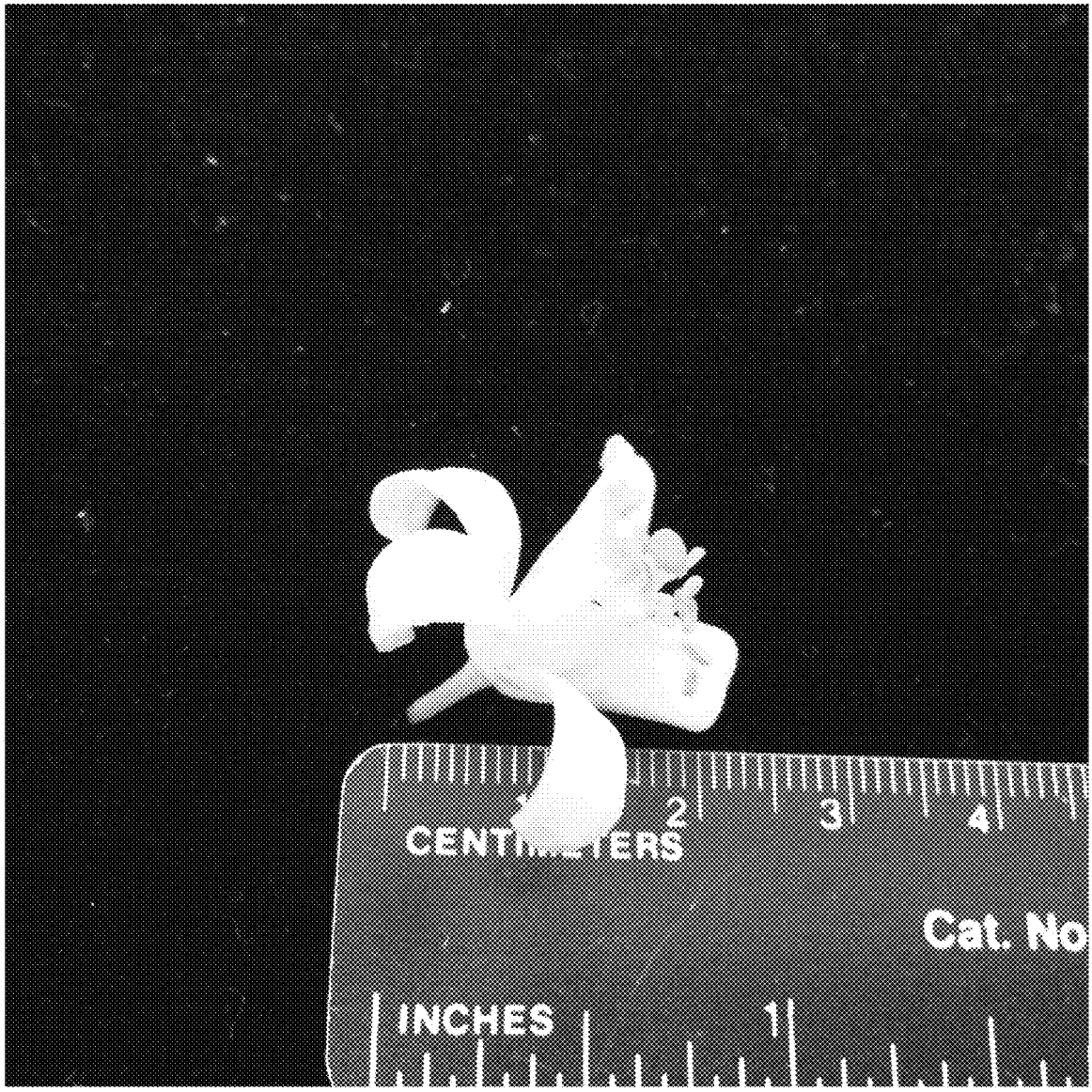
FIG. 4. Shows a close-up view of a mature 'OLL-20' flower.
Figure 5:
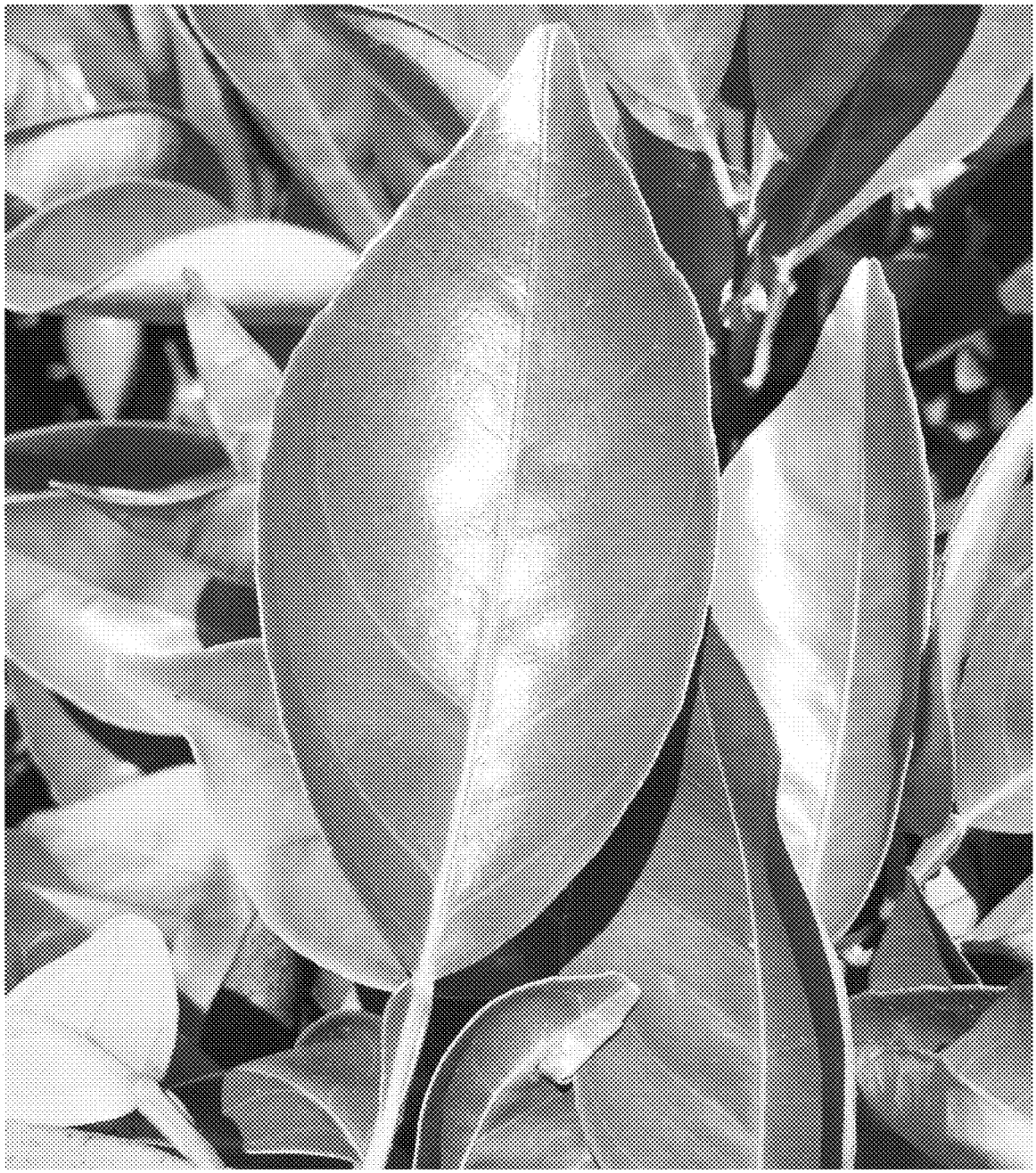
FIG. 5. Shows fully expanded view of a 'OLL-20' leaf
Figure 6:
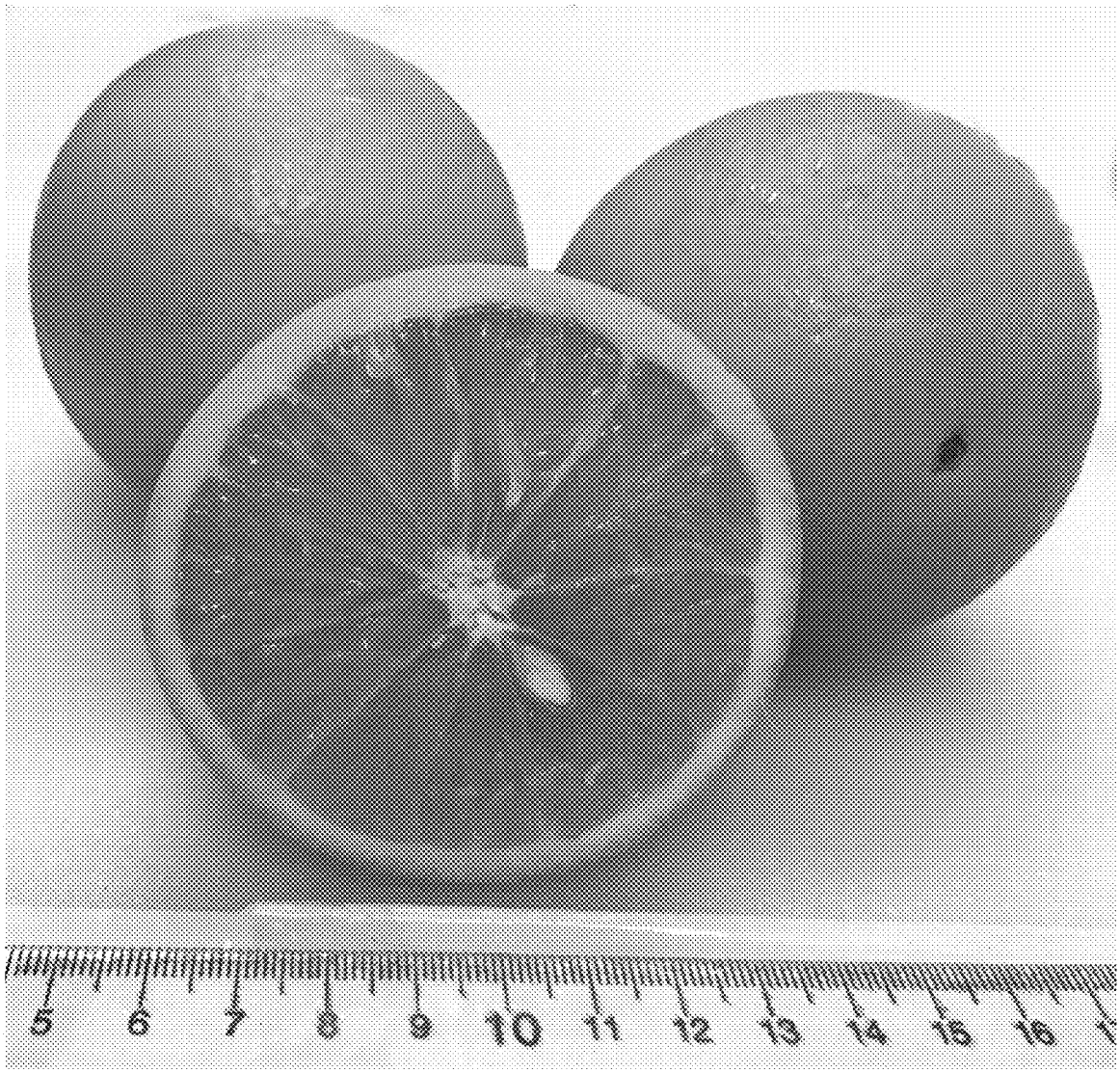
FIG. 6. Shows a close-up view of whole and cut mature fruits with seeds
Figure 7:
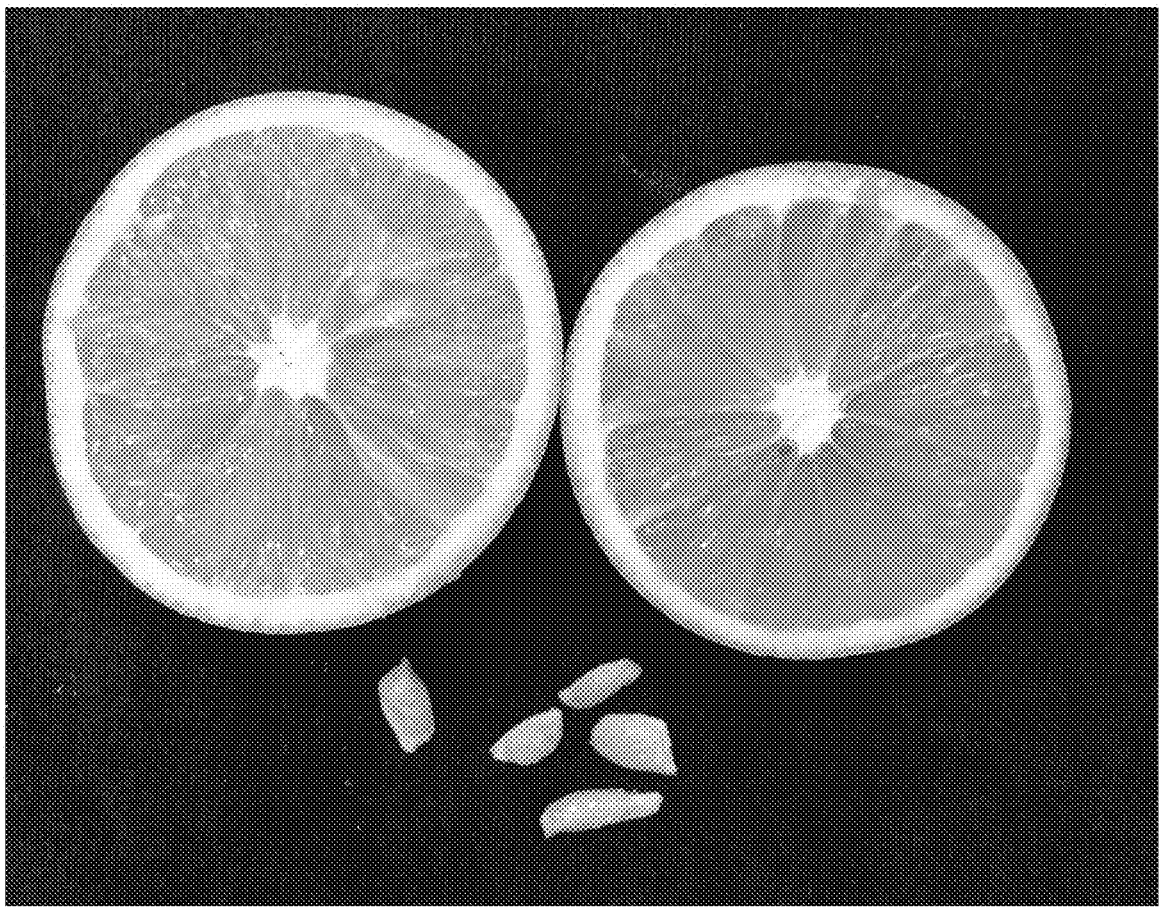
FIG. 7. Shows a close-up view of the cross section of the fruits and the seeds from mature fruits.

The following detailed description sets forth the distinctive characteristics of 'OLL-20'. The present botanical description is that of a 'OLL-20' tree approximately 5-years old grown in Florida. The colors (except those in common terms) are described from R.H.S. Colour Chart published by The Royal Horticultural Society in London (2007, 5th edition), in association with the Flower Council of Holland.

Classification:

*Botanical.*—*Citrus sinensis.*

*Common name.*—Sweet Orange.

Parentage: 'OLL' (Orie Lee Late) sweet orange tree selected by Mr. Orie Lee, believed to have originated from a 40+ year old abandoned putative USDA irradiated Pineapple sweet orange trial.

Tree:

Ploidy: Diploid.

Size: Medium.

*Width across row.*—3.5 meter.

*Width down row.*—2.95 meter on average.

Tree height: 3.05 meters.

Tree diameter: 2.84 meters in Diameter.

Tree spread: up to 3.1 meter.

Vigor: Moderate to vigorous.

Density: Canopies are quite dense.

Tree shape (form): oblate shape (obloid).

Growth habit: Vegetative growth upright, but drooping with heavy fruit load.

Trunk:

Trunk diameter: 12.6 cm at 30 cm above the ground.

Trunk texture: Smooth.

Trunk bark color: RHS N199 A (Greyed Brown).

Branches:

Branch length: 2-2.5 meters on average.

Crotch angel: Acute, with degree of 80-85 on average (less than 90 degree).

Branch texture: Relatively smooth with very small spines.

Branch color: RHS N199 A (Greyed Brown).

Spine size: 10-15 mm in length and 3 mm in diameter.

Spine color: RHS N199 B (Greyed Brown) with some RHS 138 A (Green) based on the age of the branch.

Leaves:

*Size* (*lamina average*).—Length: 122 mm on average. Width: 52 mm on average. L/W ratio: 2.3 on average. Thickness: regular and average for a typical sweet orange. Type: simple (unifoliate). Shape: Elliptical. Apex: slightly retuse. Base: acute. Margin: weakly dentate. Surface: Upper surface: smooth. Lower surface: medium vein that are pinnately netted. Color: Upper surface (adaxial): RHS 137 A (Green). Lower surface (abaxial): RHS 137 C (Green).

*Petiole.*—Shape and attachment: Brevipetiolate; shorter than leaf lamina, junction between petiole and lamina is articulate. Shape (petiole wing): narrow, obovate with narrow end at the base. Length: 15-20 mm on average. Width: 3-5 mm. Color: RHS 137 A (Green).

Flowers:
Type: Hermaphroditic
Flower bearing: (Single or cluster): Branches have flowers grown in cluster. Each cluster Consists of 2-6 flowers. Individual flowers grown from leaf terminals and leaf axillaries.
Flower diameter: Fully open flower with average diameter of 31 mm.
Flower depth: Typical flower with average depth of 12 mm.
Flower blooming period:
*First bloom*.—Usually mid- to late March in Florida.
*Full bloom*.—Usually early April.
Fragrance: Fragrant.
Flower buds size:
*Length*.—2.1 mm for the initial visible flower bud; 20.5 mm for the mature flower buds before opened.
*Diameter*.—2.2 mm in the initial visible flower bud; 7.5 mm in the mature bud.
Flower bud shape: Initial visible flower bud with round dome shape; mature flower bud with elongated olive shape.
Flower bud color (R.H.S.): 144 D (yellow-Green) for the initial visible flower bud ; RHS NN 155 A (white) for mature buds.
Reproductive organs:
Fertility: Self-fertile.
Petals:
*Number*.—5.
*Petal length*.—17.1-19 mm in average.
*Petal width*.—7.2-8 mm in average.
*Petal shape*.—Flat spatula shape.
*Apex shape*.—Smooth with obtuse angle.
*Base shape*.—Obtuse.
*Petal color*.—Upper Surface: RHS 155 B (white Group). Lower surface: RHS NN 155 A (white Group).
*Margin*.—Smooth.
Sepal:
*Number* (per flower).—3-5.
*Shape*.—Delta Shaped with acute angle at apex.
*Length*.—3.5 mm.
*Width*.—3.5 mm.
*Apex shape*.—Acute angle at apex.
*Margin*.—Smooth.
*Color*.—Upper surface: RHS 157C (Green-White). Lower surface: RHS 157B (Green-White).
Pedicel:
*Length*.—10.5 mm in average.
*Diameter*.—1.5 mm.
*Color*.—RHS 144 C (Yellow-Green).
Stamen:
*Number*.—20 per flower on average.
*Length*.—13.2.mm on average.
Anther:
*Length*.—2.5 mm.
*Width*.—0.7-1 mm.
*Color*.—RHS 11B (Yellow).
*Pollen color* (*general*).—RHS 13 A (Yellow).
*Amount of pollen*.—Abundant.
Pistil:
*Number*.—1.
*Length*.—14 mm.
*Color*.—RHS 153 B (Yellow-Green).
*Style length*.—10.2 mm.
*Style diameter*.—1.4 mm.
*Style color*.—RHS 144 D (Yellow-Green).
*Ovary shape*.—Oval shape.
*Ovary diameter*.—3.4 mm.
*Ovary color*.—RHS 143 C (Green).

Fruit:
*Size*.—Uniform.
*Average weight* (*per individual fruit*).—223.5 grams.
*Length*.—8.2 cm on average.
*Diameter*.—7.8 cm (cross section) on average.
*Shape*.—Obloid.
*Shape* (*cross-section*).—Round.
*Apex*.—Round.
*Base*.—Truncated.
*Position of the broadest part of the fruit*.—At the middle.
Harvest:
*Date of first pick*.—Late February.
*Date of last pick*.—End of May.
Fruit stem:
*Length*.—13 mm.
*Diameter*.—5 mm.
*Color*.—RHS N199 A (Greyed Brown).
Rind:
*Adherence*.—Albedo (Mesocarp) to flesh (endocarp) medium to strong.
*Thickness*.—Medium 3 mm on average.
*Texture*.—Firm.
*Surface texture*.—Relatively smooth.
*Color*.—Flavedo (epicarp): RHS 23A (Yellow Orange). Albedo (mesocarp): RHS 14 D (Yellow Orange).
*Style end*.—Closed.
*Rind oil cell density*.—83-85 cell/square cm.
*Oil gland size*.—Very small 0.7 mm.
Flesh:
*Number of segments*.—10-11.
*Segment walls* (*thickness*).—Thin to medium, soft but sufficient strength to maintain Integrity as separated.
*Juice*.—Abundant.
*Color*.—RHS 22A (Yellow Orange).
*Texture*.—Soft to medium.
*Vesicles*.—Medium thickness. Length: 12.5 -14 mm. Diameter: 2-3 mm in average.
Juice quality:
*Brix*.—12-14.
*Acidity* (*average*).—0.8-0.85.
*Ratio*.—12-18.
*Lb solid/box*.—6.5-7.2.
Seeds:
*Type*.—Polyembryonic.
*Number*.—0-5 per fruit.
*Shape*.—Clavate, some elongated Oval shape.
*Size*.—Length: 15 mm on average. Width: 7.5 mm.
*Outer surface*.—RHS 158B (Yellow-White) and slightly wrinkled.
*Inner seed coat color*.—RHS 165 C (Greyed-Orange).
*Inner surface color*.—161C (Greyed-Yellow).
*Cotyledon color*.—RHS 157C (Green-White).
*Fruit*.—Parthenocarpic.
Resistance to diseases: No obvious tree-debilitating disease problems have been observed in the trees or fruit currently grown, but systematic resistance testing has not been yet explored. *Citrus* canker lesions have been found on leaves of 'OLL-20', but with frequency and severity less than that of 'OLL-8', suggesting that its canker tolerance is similar to that of Valencia. HLB tolerance appears slightly better than that of Valencia (also supported by Tropicana).

What is claimed is:

1. A new and distinct cultivar of sweet orange tree named 'OLL-20' as illustrated and described herein.

* * * * *